(12) United States Patent
Zhang et al.

(10) Patent No.: US 8,632,466 B2
(45) Date of Patent: Jan. 21, 2014

(54) SYSTEM FOR PROCESSING PATIENT MONITORING POWER AND DATA SIGNALS

(75) Inventors: Hongxuan Zhang, Palatine, IL (US); Vincent Potenzone, Wauconda, IL (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 9 days.

(21) Appl. No.: 13/366,429

(22) Filed: Feb. 6, 2012

(65) Prior Publication Data

US 2012/0197094 A1 Aug. 2, 2012

Related U.S. Application Data

(62) Division of application No. 12/257,463, filed on Oct. 24, 2008, now Pat. No. 8,139,225.

(60) Provisional application No. 60/982,229, filed on Oct. 24, 2007.

(51) Int. Cl.
*A61B 5/00* (2006.01)
(52) U.S. Cl.
USPC .......................... 600/300; 128/904; 600/409
(58) Field of Classification Search
USPC .................................. 600/300, 409; 128/904
See application file for complete search history.

(56) References Cited

U.S. PATENT DOCUMENTS

| | | | |
|---|---|---|---|
| 5,436,553 A | 7/1995 | Pepper et al. | |
| 5,557,693 A | 9/1996 | Stevens et al. | |
| 6,243,608 B1 * | 6/2001 | Pauly et al. | 607/60 |
| 6,575,965 B1 | 6/2003 | Fitch et al. | |
| 7,079,722 B2 | 7/2006 | Mahbobi | |
| 2002/0183806 A1 * | 12/2002 | Abrahamson et al. | 607/60 |
| 2007/0237464 A1 | 10/2007 | Aronson et al. | |
| 2010/0041970 A1 * | 2/2010 | Hedberg et al. | 600/333 |

OTHER PUBLICATIONS

US Food adn Drug Administration, IBI Therapy Cool Path Ablation Catheter and IBI 1500T9 RF Generator—P060019, Mar. 16, 2007, http://www.fda.gov/cdrh/mda/docs/P060019.html.
US Food and Drug Administration, Navi-Star® Diagnostic/Ablation Deflectable Tip Catheter—P990025, Jun. 15, 2000, http://www.fda.gov/cdrh/mda/docs/p990025.html.

* cited by examiner

*Primary Examiner* — Christopher D Koharski
*Assistant Examiner* — Michael Carey
(74) *Attorney, Agent, or Firm* — Brennan K. Bradley

(57) ABSTRACT

A device interface selectively acquires patient physiological parameter data. An acquisition processor acquires physiological data from a patient. A communication processor is coupled to an optical communication pathway for receiving optical signals from a source. A conversion processor electrically coupled to the acquisition processor and communication processor converts a first optical power signal at a first frequency and received via the optical communication pathway using the communication processor, to a first electrical signal for providing power to the device interface. The conversion processor converts an optical control signal at a second frequency different from the first frequency and received via the optical communication pathway using the communication processor, to a second electrical signal for providing control data to the acquisition processor directing the acquisition processor to acquire at least one physiological parameter from a patient.

11 Claims, 5 Drawing Sheets

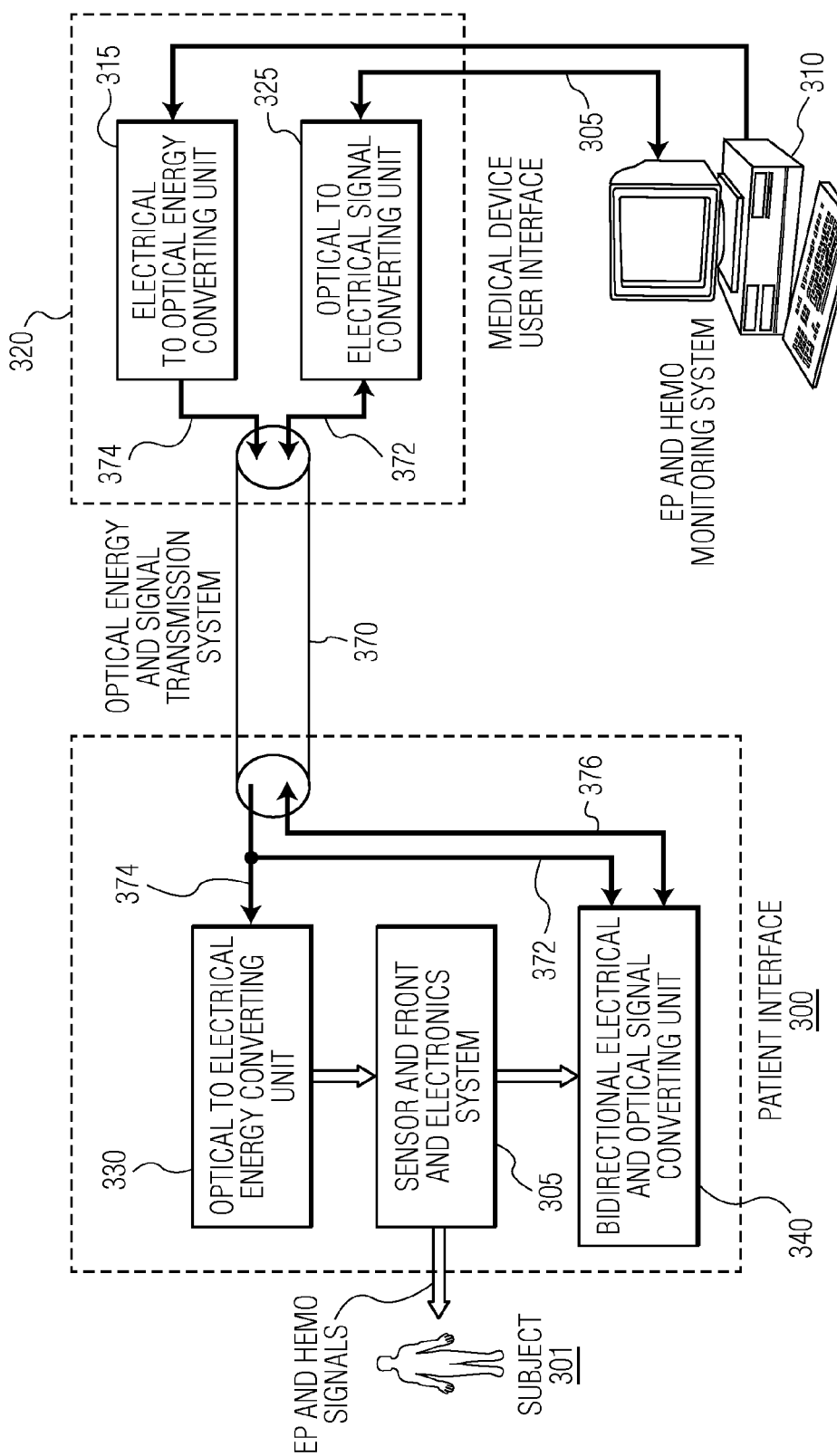

SYSTEM FOR PROCESSING PATIENT MONITORING POWER AND DATA SIGNALS

This is a divisional application of application Ser. No.: 12/257,463 filed Oct. 24, 2008 and issued on Mar. 20, 2012 as U.S. Pat. No. 8,139,225, which claims priority to provisional application Ser. No. 60/982,229 filed Oct. 24, 2007, by H. Zhang et al.

FIELD OF THE INVENTION

This invention concerns a system for combining power and operational data signals for powering and controlling the operation of a patient monitoring device.

BACKGROUND OF THE INVENTION

The operation of known medical devices requires electrical power. As used herein, a medical device includes any of patient monitoring devices for monitoring at least one physiological patient parameter and patient treatment devices enabling a healthcare professional to provide a specific mode to treatment to a patient. However, for patient and user safety, it is important that medical instruments be properly isolated to prevent patient or user contact with a high voltage power source. Typically medical devices include a transformer for providing power signal transmission between isolated and non-isolated medical devices while the data signal transmission utilizes a separate electrical circuit. A drawback associated with this known setup for monitoring and treating patients is the signal transmission distance able to be traversed and noise effects over the signal transmission line. Thus, known medical devices typically include two types of circuits and produce substantial noise induced signal distortion associated with a patient monitoring data signal transmitted between a sensor and monitoring unit.

Known medical devices utilize different kinds of strategies for isolation and transmission of power, analogue signals, and digital signals, such as use of a transformer/magnet for power transmission, optical diode for digital signal isolation and transmission, for example. The necessity of the different kind circuits (power transfer and data/command transmission) and complexity of the hardware structure and construction limits clinical usage and risks voltage/current leakage. Known medical systems typically involve:

1. Different isolation and signal transmission strategies involving complex hardware and isolation requirements. Hence, potential risk of voltage/current leakage is increased impacting safety. Further, in medical devices, high voltage isolation (between 3000V-6000V) is required to ensure safety of both patient and user during clinical patient monitoring and treatment.
2. Power and data transmission utilizing electrical and magnetic devices, such as transformers. This kind of the transmission involves electrical-magnetic noise/interference, such as electrostatic discharge (ESD) and/or electromagnetic compatibility-based noise (EMC), for example.
3. Current strategies for continuous power and real time data signal/command signal transmission employ electrical cables, such as low voltage differential signaling cables (LVDS), Serial, USB and the like. However, use of these signaling cables decreases the transmission distance for power and signal transmission since the electrical capacitor and impedance may cause attenuation for both power and signal resulting in data transmission error. For example, Cat 6 cable based LVDS communication is typically good for use up to 40 meters. Beyond 40 meters, the efficiency of power transfer and reliability of the signal transmission is reduced.
4. Electrical cables for power and data signal/command signal transmission have a limited bandwidth resulting in limited transmission data rate. Moreover, power and data cables are typically separated from one another to prevent detrimental effects associated with noise from either cable.

Therefore, a need exists to provide a data and power signal transmission method and system to reduce noise, enable increased power/data signal transmission distances, improve data quality and reliability while providing improved safety for patients and users. A system according to invention principles addresses these deficiencies and related problems.

SUMMARY OF THE INVENTION

A device interface selectively acquires patient physiological parameter data. An acquisition processor acquires physiological data from a patient. A communication processor is coupled to an optical communication pathway for receiving a plurality of optical signals from a source. A conversion processor is electrically coupled to the acquisition processor and communication processor and converts a first optical power signal at a first frequency and received via the optical communication pathway using the communication processor, to a first electrical signal for providing power to said device interface. The conversion processor converts an optical control signal at a second frequency different from the first frequency and received via the optical communication pathway using the communication processor, to a second electrical signal for providing control data to the acquisition processor directing the acquisition processor to acquire at least one physiological parameter from a patient.

BRIEF DESCRIPTION OF THE DRAWINGS

FIG. 3 is a functional block diagram of the optical power and data signal transmission system according to invention principles;

DETAILED DESCRIPTION OF THE INVENTION

Figure 2:
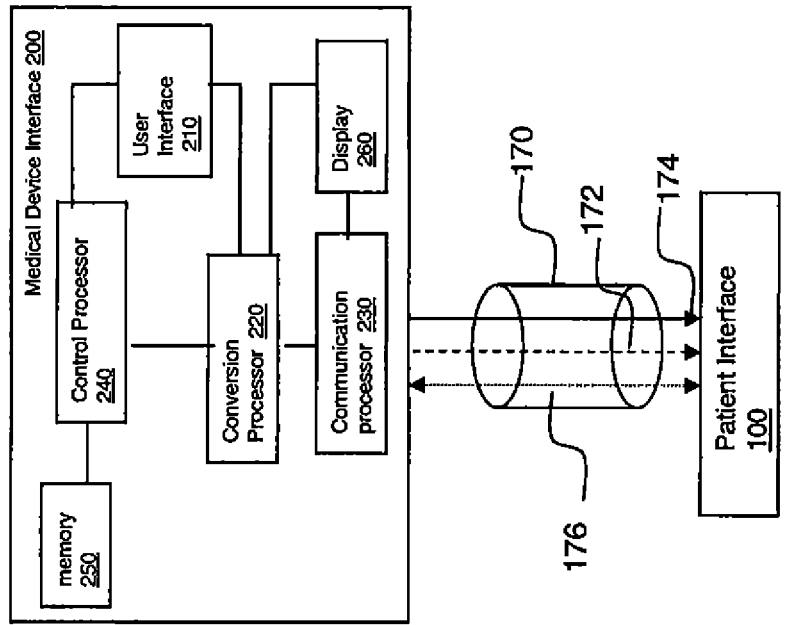
FIG. 2 is a block diagram of a medical device interface according to invention principles.

A system acquires at least one patient physiological parameter and monitors the acquired parameter using a bidirectional concurrent optical transmission of control, data and power signals. The system combines the communication of power signal, patient data signals and medical device control signals for transmission via the same optical communication pathway, for example a fiber optic communication pathway. A power signal as used herein is either an electrical (AC or DC) or optical signal that provides power for powering at least one medical device. A patient data signal is an electrical or optical signal including data representing a physiological parameter of a patient that is acquired from a sensor connected to or within a patient. The patient data signal may be representative of electrophysiological data and/or hemodynamic data. A medical device control signal is any of an electrical or optical signal and includes data representing control information conditioning a patient sensor of a particular medical device to operate in a desired manner. The medical device control signal is automatically selected in response to a trigger event or derived from user input. The optical communication pathway is a communication pathway able to transmit at least one optical energy signal between electrically isolated and non-electrically isolated devices. The optical communication pathway includes any of a single mode or multimode fiber optic link. The system advantageously improves medical diagnostic capability by extending the distance between a medical device for acquiring patient parameters and a medical device interface for monitoring the acquired patient data. Moreover, the conversion from electrical energy signals to optical energy signals provide improved mechanisms for treating patient conditions, for example treatment of cardiac arrhythmias, such as optical ablation for atrial fibrillation. Additionally, the system reduces noise and facilitates medical power/signal transmission and control with improved safety for clinical patients and healthcare professionals and less current leakage/noise effects. Furthermore, the system which concurrently and bidirectionally transmits power and non-power (patient data and/or control signals) while improving the signal fidelity of data signals transmitted for monitoring.

The system provides:

Improved voltage isolation and reduced current leakage for both power signals and data/command signal transmission pathway. This increases medical device safety, especially in patient monitoring/recording/treatment devices and in operating rooms with safety risk typically being associated with using either an ablator or a defibrillator.

Reduced spurious electrical noise and artifacts effects. There is no energy or signal/noise emission from optical signal transmission. Moreover, environmental noise, such as EMC/EMI/ESD from other devices, will not be able to affect the quality of the power and data/command signal transmission in the optical system.

Modulated light transfer in multi-channel optical fiber. This reduces power and signal attenuation rate which increase transmission distance and efficiency.

Increases transmitted data rate via the optical communication pathway. This is particularly advantageous in the case of multi-channel patient data and medical device control signal being transferred concurrently and bilaterally.

Reduces size of a transmission cable needed for bidirectional transmission of power and data.

A processor as used herein is a device for executing stored machine-readable instructions for performing tasks and may comprise any one or combination of, hardware and firmware. A processor may also comprise memory storing machine-readable instructions executable for performing tasks. A processor acts upon information by manipulating, analyzing, modifying, converting or transmitting information for use by an executable procedure or an information device, and/or by routing the information to an output device. A processor may use or comprise the capabilities of a controller or microprocessor, for example. A processor may be coupled (electrically and/or as comprising executable components) with any other processor enabling interaction and/or communication therebetween. A user interface processor or generator is a known element comprising electronic circuitry or software or a combination of both for generating display images or portions thereof. A user interface comprises one or more display images enabling user interaction with a processor or other device.

An executable application, as used herein, comprises code or machine readable instructions for conditioning the processor to implement predetermined functions, such as those of an operating system, a context data acquisition system or other information processing system, for example, in response to user command or input. An executable procedure is a segment of code or machine readable instruction, sub-routine, or other distinct section of code or portion of an executable application for performing one or more particular processes. These processes may include receiving input data and/or parameters, performing operations on received input data and/or performing functions in response to received input parameters, and providing resulting output data and/or parameters. A user interface (UI), as used herein, comprises one or more display images, generated by a display processor and enabling user interaction with a processor or other device and associated data acquisition and processing functions.

The UI also includes an executable procedure or executable application. The executable procedure or executable application conditions the display processor to generate signals representing the UI display images. These signals are supplied to a display device which displays the image for viewing by the user. The executable procedure or executable application further receives signals from user input devices, such as a keyboard, mouse, light pen, touch screen or any other means allowing a user to provide data to a processor. The processor, under control of an executable procedure or executable application, manipulates the UI display images in response to signals received from the input devices. In this way, the user interacts with the display image using the input devices, enabling user interaction with the processor or other device. The functions and process steps herein may be performed automatically or wholly or partially in response to user command. An activity (including a step) performed automatically is performed in response to executable instruction or device operation without user direct initiation of the activity. Workflow comprises a sequence of tasks performed by a device or worker or both. An object or data object comprises a grouping of data, executable instructions or a combination of both or an executable procedure.

Figure 1:
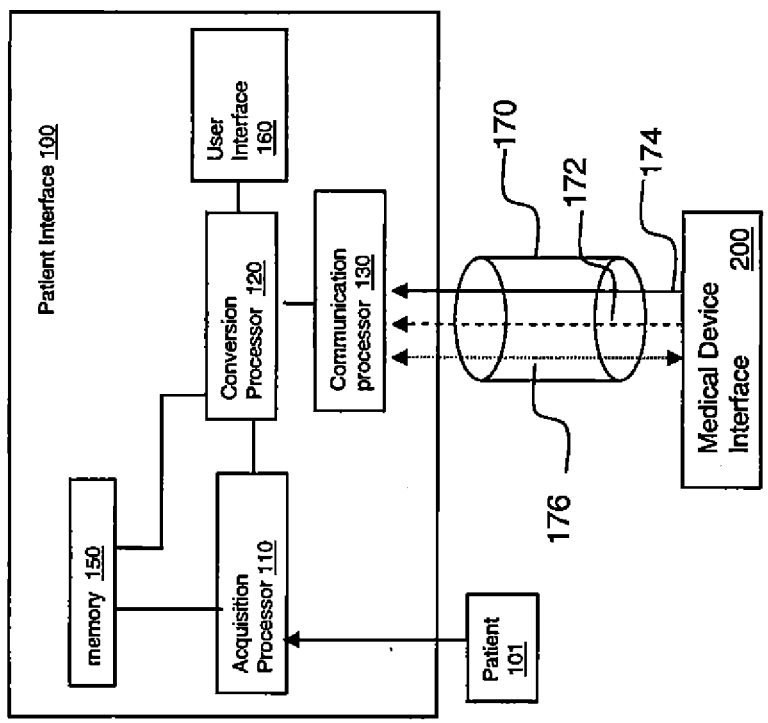
FIG. 1 is a block diagram of a patient device interface according to invention principles.

An embodiment of the system is shown in the block diagram of FIG. 1. The system includes a patient device interface 100 that is connected to a patient 101 for acquiring at least one physiological parameter of a patient and a medical device interface 200 located remotely from the patient device interface 100 for controlling operation of patient interface device 100 and monitoring the acquired physiological parameter(s). An optical communication pathway (link) 170 is connected between the patient device interface 100 and medical device interface 200 for selectively transmitting multiple optical signals therebetween. FIG. 2 illustrates an embodiment of medical device interface 200.

Patient device interface 100 includes conversion processor 120 for automatically converting a signal received in a first format into a signal having a different second format. Conversion processor 120 is an electrical circuit that automatically converts electrical signal into optical signals and automatically converts optical signals into electrical signals. Alternatively, conversion processor 120 may have hard coded instructions directing operation of at least one executable application to control external circuitry to convert signals between optical signals and electrical signals and vice versa. The conversion between optical and electrical signals is performed in a known manner. Exemplary ways of converting power between optical power and electrical power (and vice versa) include directly converting AC or DC electrical power into optical power (light). The conversion is dependent on the bandwidth characteristics of the optical fiber through which the optical power will be transmitted and thus may require tuning of the optical wavelength to particular frequencies to maximize efficiency. Alternatively conversion between electrical and optical power is performed using an optical converter that converts electrical power into a laser beam and light to be transmitted via optical fiber. The conversion between optical and electrical power includes an optical collecting unit that amplifies (focuses) the received laser beam to convert the light into electrical power. A rectifier and other known filtering methods to achieve a stable and constant current are provided enabling the converted electrical power to be used in powering a patient device interface, for example.

Communication processor 130 is coupled between conversion processor 120 and optical communication pathway 170. Communication processor 130 receives multiple optical input signals 172 and 174 (discussed below) from a source medical device interface 200. Communication processor 130 further transmits at least one optical data signal 176 including data representing at least one patient physiological parameter derived from a patient to the medical device interface 200 for monitoring. Additionally optical data signal 176 is a bidirectionally transmitted data signal transmitted between patient interface device 100 and medical device interface 200. Thus, communication processor 130 is conditioned for bidirectional concurrent communication of multiple optical energy signals between the patient device interface and a medical device interface used in monitoring patient parameters. Additionally, the optical communication pathway 170 over which the optical input signals 172 and 174 and bidirectional data optical data signal 176 are transmitted may comprise a single optical communication link, a single optical fiber channel or multiple optical communication links.

First optical input signal 174, transmitted at a first frequency, is a power signal for providing power to patient device interface 100. Optical power signal 174 is received by communication processor 130 and provided to conversion processor 120 for conversion from optical power signal to an electrical power signal. Conversion processor 120 further provides the electrical power derived from optical power signal 174 to system components for providing power and enabling patient interface device to operate. Second optical input signal 172 is transmitted at a second frequency different from the first frequency and is a control signal including data for controlling the operation of patient device interface 100. The optical control data signal 172 includes data for directing the acquisition processor 110 to acquire at least one physiological patient parameter. As described with respect to FIG. 1, the transmission of optical power signal 174 and optical control signal 172 originates from medical device interface 200 and is received by communication processor 130 of patient device interface 100.

Acquisition processor 110 is electrically coupled to conversion processor 120 and acquires data representing at least one physiological parameter from patient 101. Data acquired by acquisition processor 110 includes any of (a) ECG data, (b) ICEG data (c) IBP data, (d) ventilator data and (e) SPO2 data. These types of medical data are merely exemplary and any parameter able to be acquired or sensed may be acquired by patient device interface 100. Operation of acquisition processor 110 is selectively controlled by data in optical control data signal 172. Optical control data signal 172 includes data directing the operation of acquisition processor 110. Optical control data signal 172 includes data directing the type of parameter data to be acquired from patient 101 by acquisition processor 110. Upon receipt of optical control data signal 172, communication processor 130 provides optical control data signal 172 to conversion processor 120 for conversion into a second electrical signal to direct operation of acquisition processor 110. Alternatively, optical control data signal 172 is provided from communication processor 130 to acquisition processor 110 for directing operation of acquisition processor 110 in acquiring patient parameter data from patient 101. A memory 150 coupled to acquisition processor 110 and conversion processor 120 and provides a buffer to facilitate real-time acquisition of patient data.

Upon acquiring data representing at least one patient physiological parameter, acquisition processor 110 generates an electrical data signal including the acquired data and provides the acquired data to conversion processor 120. Conversion processor 120 automatically converts an electrical data signal into optical data signal 176. Optical data signal 176 in one embodiment has a frequency different from the frequencies of the optical control signal 174 and optical power signal 172. Optical data signal 176 is provided to communication processor 130 for communication to medical device interface over optical link 170. Optical data signal 176 includes patient data to be monitored and analyzed by a healthcare professional. For example, if patient device interface is an electrocardiogram sensor, the data acquired is electrophysiological data representing characteristics of patient heart activity. This data is converted into an optical data signal and communicated to the medical device interface 200 for monitoring.

Patient device interface 100 further includes a user interface 160 enabling a user to selectively control the operation of the patient device interface 100. User interface 160 enables a healthcare professional to modify the operational control of patient interface 100 and select procedures that supplement or modify control data received in optical control signal 172.

As shown in FIG. 2, medical device interface 200 and includes similar elements that operate in similar manner to the corresponding elements described in FIG. 1. For example, conversion processor 220 and communication processor 230 operate in like manners. However, the operation of medical device interface 200 differs from the patient device interface 100 and those differences are described herein.

Medical device interface 200 includes a control processor 240 coupled between a memory 250 and a user interface 210. User interface 210 comprises selectable switches, knobs, buttons and/or a touch-screen display screen providing user selectable image elements for initiating execution of at least one executable application causing control processor 240 commanding response to instruction in memory 250 to direct operation of patient device interface 100. A healthcare provider interacts with user interface 210 to selectively determine operational instructions including control data directing operation of patient device interface 100. Control data includes (a) type of patient parameter acquired; (b) number of patient parameters acquired; (c) duration of patient parameter acquisition; and/or (d) trigger event data indicating an action be performed in response to acquired data. Control data is provided to conversion processor 220 and automatically converted into an optical control signal 172 having a first frequency. Optical control signal 172 is provided to communication processor 230 and communicated to patient device interface 100 via optical communication link 170 for controlling patient device interface as described above.

Conversion processor 220 is coupled to a power source (not shown) which provides electrical power to medical device interface 200. Conversion processor 220 draws on electrical power and converts electrical power into an optical power signal 174. Optical power signal 174 is provided to communication processor 230 which communicates optical power signal 174 via optical communication pathway 170 and provides power to the patient device interface 100.

Upon powering and directing the operation of patient device interface 100, patient parameter data is acquired by acquisition processor (110 in FIG. 1), converted into an optical data signal 176 and communicated via optical communication pathway 170 to medical device interface 200. Communication processor 230 receives the optical data signal 176 and provides the optical data signal 176 to conversion processor 220 for conversion into a desired medical data format for at least one of (a) monitoring of a patient and (b) storage in a storage medium. Monitoring of a patient comprises analyzing patient data, communicating patient data to a hospital information system (HIS) or clinical information system (CIS), displaying patient parameter data on a display 260 or outputting parameter data in the desired medical data format as a hardcopy. Medical data format includes data formatted in, without limitation, a Medical Interface Bus (MIB) compatible format, DICOM, an Internet Protocol (I.P.) data format, an IEEE bus compatible protocol, and a Health Level Seven (HL7) protocol, XML, HTTP and HTTPS.

FIG. 3 is a functional block diagram of an embodiment of the system. The system includes medical device interface 310 as a personal computer having a user interface able to selectively receive user input. The medical device interface 310 is connected to and controls the conversion processor 320 via a communication network 305. Communication network 305 is any hardwired or wireless communication network enabling power and/or data transmission between medical device interface 310 and conversion processor 320. Herein, conversion processor 320 includes an electrical-to-optical power conversion unit 315 that automatically converts electrical power into an optical power signal 374. Conversion processor 320 further includes an optical-to-electrical signal converting unit 325 for converting control data derived from user input and for directing the operation of the patient device interface 300 to acquire patient physiological parameter data from a patient. Control data is provided as an electrical signal and is converted by optical-to-electrical signal converting unit 325 into an optical control signal 372. Optical power signal 374 and optical control signal 372 are communicated via optical communication pathway 370 for receipt by the patient device interface 300. Optical power signal 374 and optical control signal 372 have different frequencies and are communicated concurrently along the same fiber. Optical signal transmission at different frequencies advantageously enables the signals to be isolated from one another. Thus, data and power are transmitted together along the same pathway without cross talk problems.

Optical power signal 374 is received by a second optical-to-electrical power converting unit 330 for automatically converting the optical power into electrical power for powering operation of the patient device interface 300. Converted electrical power is applied to acquisition processor 305 which includes a sensor for sensing a patient physiological parameter and associated interface electronics. The sensor is an electrophysiological sensor and/or a hemodynamic sensor that contacts the surface of the patient or is conditioned for intra-patient monitoring, for example. Optical control signal 372 is received by a bidirectional electrical-to-optical conversion unit 340. Conversion unit 340 converts the optical control signal including control data into an electrical control signal (analog or digital) and directs the operation of acquisition processor 305 in acquiring a patient parameter. A sensor acquires data representing the physiological parameter and provides the acquired data to conversion unit 340 which automatically converts the acquired data signal into an optical data signal 376 to be communicated back to medical device interface 310 via the optical communication pathway 370. While conversion units 330 and 340 are shown as separate components, one skilled in the art may readily recognize that the relevant circuitry is combinable into a single element such as denoted by conversion processor 120 in FIG. 1.

It should be noted that the data included in optical data signal 376 and received by medical device user interface for monitoring of a patient may be used to trigger additional actions that are automatically undertaken by the medical device interface 310 or provide a warning to a healthcare professional that a certain condition is occurring and intervention by a healthcare professional is necessary. For example, in the case where patient device interface 300 is an ECG processing device and ECG data indicates that a patient may be ischemic, a notification maybe provided to a nurse or doctor at a central monitoring station that a patient should be attended to. Alternatively, if the optical data signal 376 includes data indicating an early onset of a particular condition, medical device interface 310 automatically modifies control data being communicated as optical control signal 372 to instruct the acquisition processor 305 of patient device interface 300 to change at least one of (a) type and/or number of parameters being monitored; (b) intervals at which parameters are being monitored or (c) duration of monitoring of the parameter.

Alternatively, patient device interface 300 may include a treatment module for providing a treatment to a patient. For example, in an intra-cardiac catheter system, by receiving and analyzing intra-cardiac parameters, laser heating and burning treatment can be utilized for treating cardiac arrhythmia, such as atrial fibrillation (AF). Thus, the system is not limited to optical signal and power transmission, but also supports combination of optical and electrical power and signal transmission and control of a treatment module. A further embodiment includes a catheter connected to patient device interface 300 and enables both electrophysiological signal sensing/recording and optical (laser) ablation strategies. The electrophysiological signals sensing, analysis and optical ablation is constructed as a closed loop for automatic monitoring and arrhythmia treatment. Thus, upon receiving an optical data signal 376 indicating that the catheter has sensed an arrhythmia, medical device interface 310 automatically modifies (and/or replaces) control data used in generating optical control signal 372 to cause the catheter to perform ablation thus treating the patient. An optical ablation procedure is safer due to absence of voltage and current leakage, is more efficient in view of the precise pathological tissue localization and ablation point, and is more reliable because of the time and energy for ablation power delivery are related to the severity of the pathology on the corresponding accurate tissue points.

Figure 4:
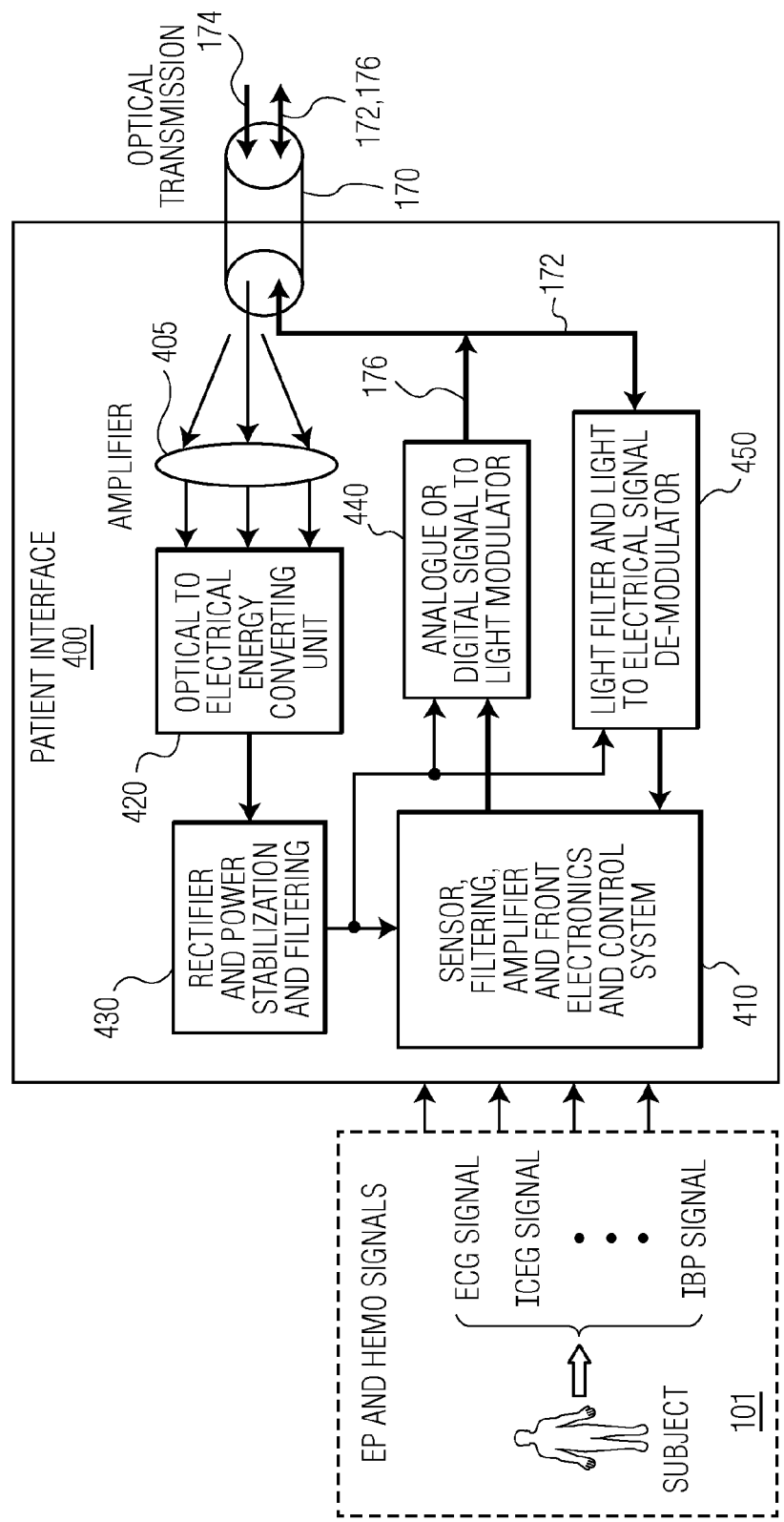
FIG. 4 is a functional block diagram of an exemplary patient device interface according to invention principles.
Figure 5:
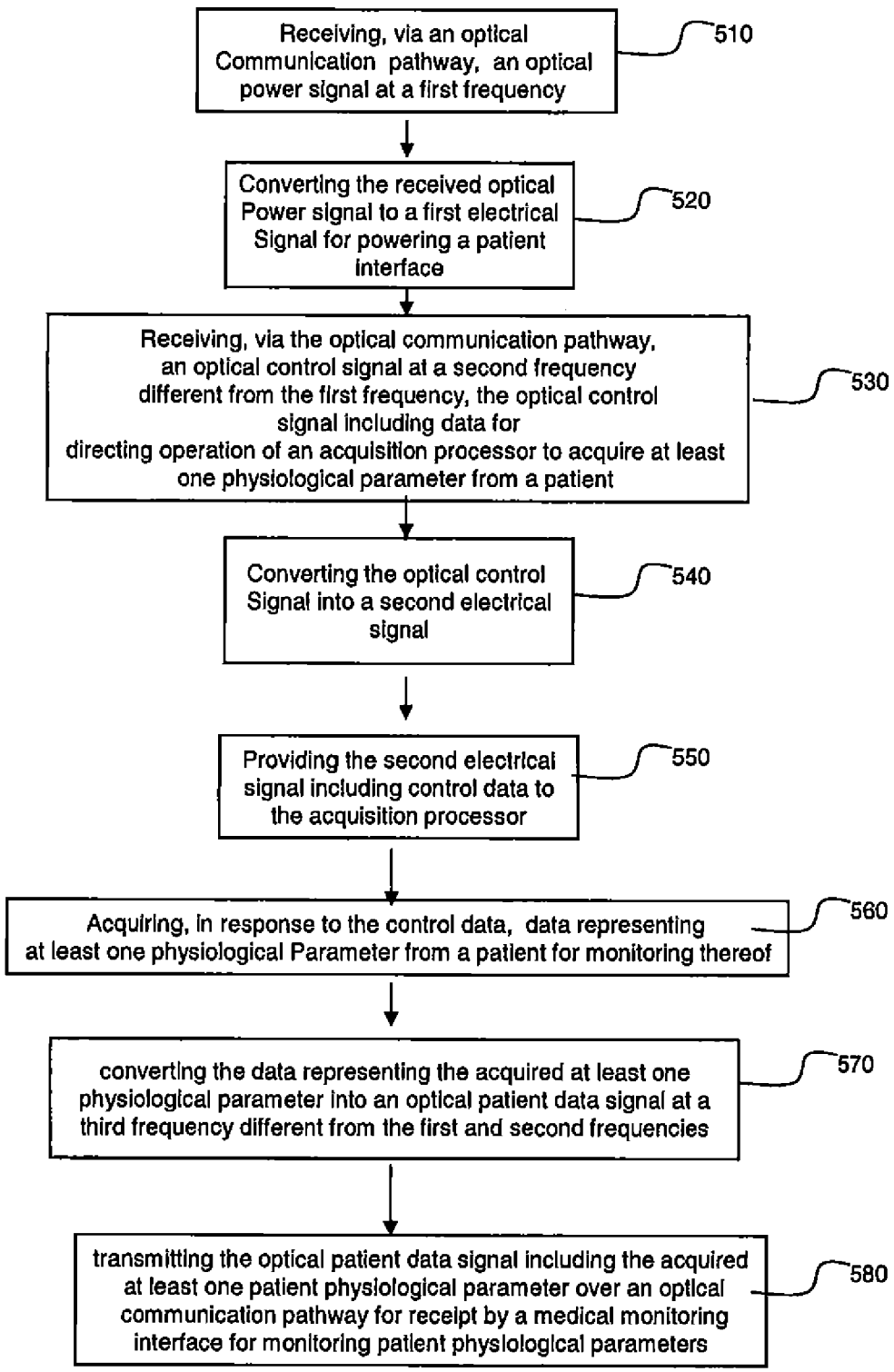
FIG. 5 is a flow diagram detailing the operation of the patient device interface according to invention principles.

FIG. 4 provides a detailed function block diagram of the operation of an exemplary patient device interface 400 in acquiring physiological parameter data from patient 410. Patient device interface 400 is in communication with an exemplary medical device interface (200 in FIG. 2). Optical power signal 174 is received over optical communication link 170. Amplifier 405 amplifies optical power signal 174 and provides the amplified signal to optical-to-electrical conversion unit 420 whereby the optical power signal is converted into electrical power signal. The electrical power signal is provided to a rectifier/power stabilizer 430 which convert the electrical power from AC to DC and also provides a stabilized (constant) output of the DC electrical power in order to provide adequate power to the components of the patient device interface 400. Particularly, electrical power is provided to the acquisition processor 410 (described above) which acquires data representing patient physiological parameter(s). Concurrently with power conversion, optical control signal 172 is received by a light filter and light-to-electrical signal demodulator 450 which demodulates the optical control signal 172 into an electrical control signal for controlling the operation of acquisition processor 410 and directing acquisition of patient parameter data. Upon acquisition of patient parameter data, an electrical data signal including patient parameter data is provided to light modulator 440 for conversion from an electrical data signal (analogue or digital) to optical data signal 176. Electrical-to-light modulator 440 may comprise an analogue or digital signal modulator enabling automatic conversion of analogue or digital data signals into optical data signals. Optical data signal 176 is communicated to medical device interface 200 (FIG. 2) for monitoring of the acquired patient parameters. Optical communication pathway 170 enables concurrent transmission of power, control and data signals at different frequencies and conveys signals in a substantially mutually isolated manner and isolated from spurious environmental electrical noise. Moreover, the optical transmission of power reduces noise or electromagnetic interference originating from patient interface devices enabling use of these devices in areas that heretofore were inaccessible FIG. 5 is flowchart of a process performed by patient device interface 100. At step 510, device interface 100 receives, via an optical communication pathway, an optical power signal at a first frequency. The received optical power signal is converted to a first electrical signal for powering the device interface in step 520. An optical control signal having a second frequency different from the first frequency is received via the optical communication pathway at step 530. The optical control signal received at step 530 includes control data for direction operation of an acquisition processor to acquire at least one physiological parameter from a patient. The activities in steps 510 and 530 are performed, for example, using a communication processor connected to the optical communication pathway. The optical control signal is converted into a second electrical signal in step 540 and the electrical control data signal is provided to the acquisition processor at step 550. In response to the control data, data representing at least one physiological parameter is acquired and used in monitoring the patient as in step 560. In step 570, data representing the acquired patient physiological parameter is converted into an optical patient data signal at a third frequency different from the first and second frequencies. The optical patient data signal including the acquired at least one patient physiological parameter is transmitted, in step 580, over an optical communication pathway for receipt by a medical monitoring interface for monitoring patient physiological parameters.

Figure 6:
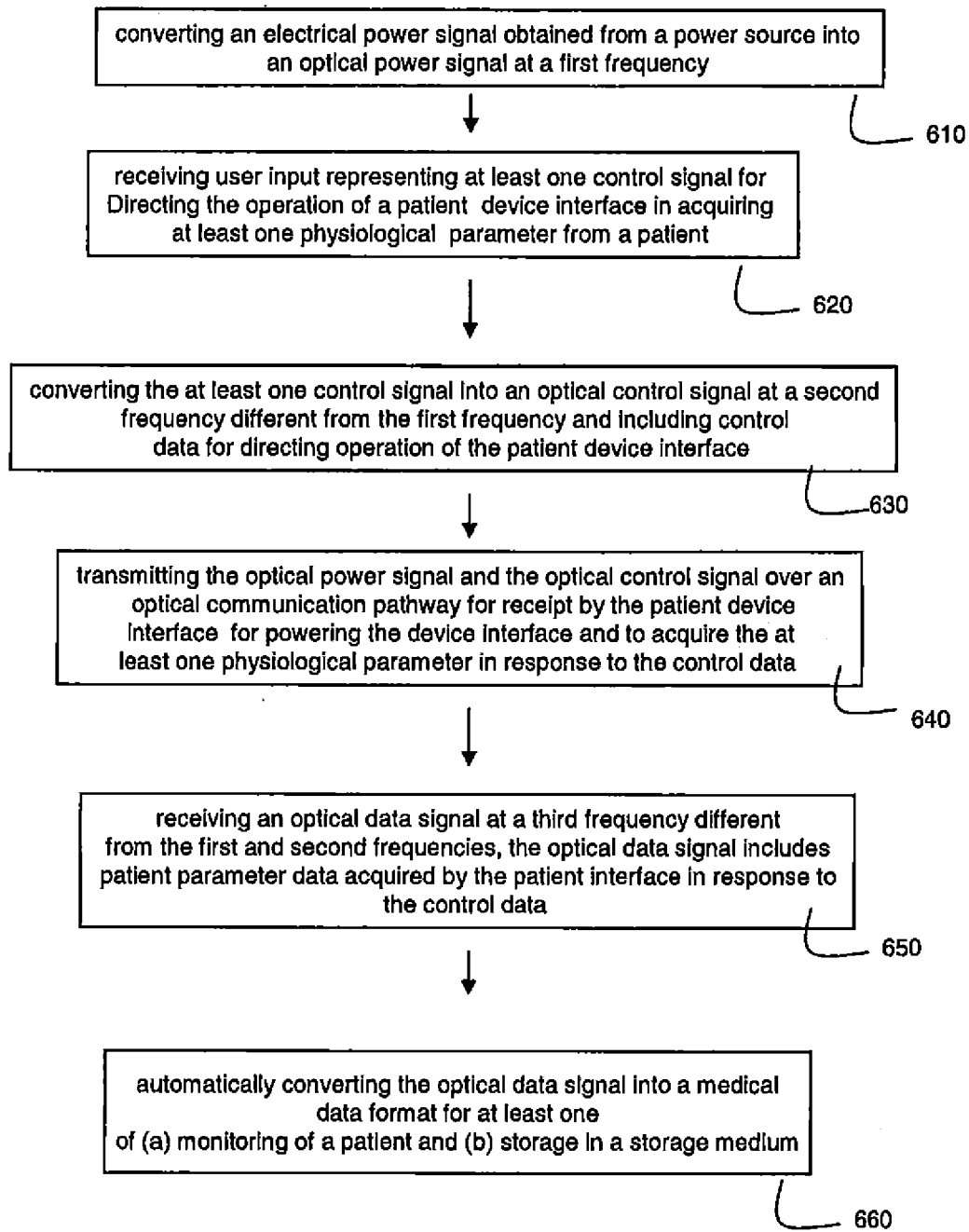
FIG. 6 is a flow diagram detailing the operation of the medical device interface according to invention principles according to invention principles.

FIG. 6 is a flowchart of a process performed by the medical device interface. At step 610, an electrical power signal derived from a power source is converted into an optical power signal having a first frequency. User input representing at least one control signal for directing the operation of a patient device interface in acquiring at least one physiological parameter from a patient is received in step 620. The control signal is converted into an optical control signal at a second frequency different from the first frequency in step 630. The optical control signal includes data for directing the operation of the patient device interface. In step 640, the optical power and optical control signals are transmitted, substantially concurrently, over an optical communication pathway for receipt by the patient interface for powering the patient device interface and to acquire the at least one physiological parameter in response to the control data. In step 650, the medical device interface further receives an optical data signal at a third frequency, different from the first and second frequencies, which include patient parameter data acquired by the patient device interface in response to the control data. The optical data signal is automatically converted in step 670 into a medical data format for at least one of (a) monitoring of a patient and (b) storage in a storage medium.

The systems and processes described are not exclusive. Other systems and processes are derived in accordance with the principles of the invention to accomplish the same objectives. Although this invention has been described with reference to particular embodiments, it is to be understood that the embodiments and variations shown and described herein are for illustration purposes only. Modifications to the current design may be implemented by those skilled in the art, without departing from the scope of the invention. The processes and applications may, in alternative embodiments, be located on one or more (e.g., distributed) processing devices accessing a network linking the elements of FIGS. 1-6. Further, any of the functions and steps provided in FIGS. 1-6 may be implemented in hardware, software or a combination of both and may reside on one or more processing devices located at any location of a network linking the elements of FIGS. 1-6 or another linked network, including the Internet.

What is claimed is:

1. A medical device user interface for selectively monitoring patient physiological parameter data comprising:
a user interface for receiving user entered command data representing at least one control signal for controlling the operation of a device interface in acquiring at least one physiological parameter from a patient;
a conversion processor electrically coupled to said user interface for
converting an electrical power signal obtained from a power source into an optical power signal having a first frequency; and
converting said at least one control signal received from said user interface into an optical control signal having a second frequency different from said first frequency, said optical control signal including control data for controlling the device interface; and
a communication processor electrically coupled to said conversion processor for transmitting said optical power signal and said optical control signal via an optical communication pathway for receipt by the device interface.

2. The medical device interface according to claim 1, wherein
said communication processor selectively receives an optical data signal at a third frequency different from said first and second frequencies, said optical data signal includes patient parameter data acquired by the device interface, and
said conversion processor automatically converts said optical data signal into a medical data format for at least one of (a) monitoring of a patient and (b) storage in a storage medium.

3. The medical device interface according to claim 2, further comprising
a display electrically coupled to said conversion processor for displaying said patient parameter data in said medical data format.

4. The medical device interface according to claim 2, further comprising
a patient monitoring unit electrically coupled to said conversion processor for receiving said patient parameter data in said medical data format and automatically notifying a user if said acquired patient parameter data exceeds a threshold value.

5. The medical device interface according to claim 1, wherein said optical power signal and said optical control signal are substantially isolated from each other and spurious electrical noise.

6. The medical device interface according to claim 2, wherein said optical power signal, said optical control signal and said optical data signal are substantially isolated from each other and from spurious electrical noise.

7. The medical device interface according to claim 2, wherein said communication processor is conditioned for bidirectional simultaneous communication of a plurality of optical energy signals between said medical device interface and said device interface.

8. The medical device interface according to claim 1, wherein said optical power signal and said optical control signal are transmitted over a single optical link.

9. The device interface according to claim 2, wherein said optical power signal and said optical control signal are transmitted over and said optical patient data signal is received over a single optical link.

10. A method for monitoring patient physiological parameter data comprising the activities of:

converting an electrical power signal obtained from a power source into an optical power signal at a first frequency;

receiving user input representing at least one control signal for directing the operation of a device interface in acquiring at least one physiological parameter from a patient;

converting the at least one control signal into an optical control signal at a second frequency different from the first frequency and including control data for directing operation of the device interface; and transmitting the optical power signal and the optical control signal over an optical communication pathway for receipt by the device interface for powering the device interface and to acquire the at least one physiological parameter.

11. The method according to claim 10, further comprising the activities of receiving an optical data signal at a third frequency different from the first and second frequencies, the optical data signal includes patient parameter data acquired by the device interface in response to the control data, and automatically converting the optical data signal into a medical data format for at least one of (a) monitoring of a patient and (b) storage in a storage medium.

* * * * *